United States Patent [19]

Mastri et al.

[11] Patent Number: 5,531,763
[45] Date of Patent: Jul. 2, 1996

[54] SUTURE CINCHING APPARATUS

[75] Inventors: Dominick L. Mastri, Bridgeport; Michael S. Kolesa, Norwalk; Thomas R. Hessler, Danbury, all of Conn.

[73] Assignee: United States Surgical Corporation, Norwalk, Conn.

[21] Appl. No.: 319,912

[22] Filed: Oct. 7, 1994

[51] Int. Cl.⁶ .................................................. A61B 17/04
[52] U.S. Cl. ..................... 606/148; 606/147; 606/228; 606/232; 29/750; 72/409.08
[58] Field of Search ........................... 606/147, 148, 606/151, 228, 232; 29/270, 280, 283.5, 749, 751, 750, 753; 72/409, 410

[56] References Cited

U.S. PATENT DOCUMENTS

| | | |
|---|---|---|
| 462,270 | 11/1891 | McConnaughey . |
| 1,461,524 | 7/1923 | Goddard . |
| 1,669,537 | 5/1928 | Schaffer . |
| 3,409,014 | 11/1968 | Shannon . |
| 3,541,591 | 11/1970 | Hoegerman . |
| 3,802,438 | 4/1974 | Wolvek . |
| 3,831,608 | 8/1974 | Kletschka et al. . |
| 3,857,396 | 12/1974 | Hardwick . |
| 3,910,281 | 10/1975 | Kletschka et al. . |
| 4,016,883 | 4/1977 | Wright, Jr. . |
| 4,173,067 | 11/1979 | Steiner et al. ............................ 29/749 |
| 4,291,698 | 9/1981 | Fuchs et al. . |
| 4,381,785 | 5/1983 | Robbins . |
| 4,387,489 | 6/1983 | Dudek . |
| 4,632,101 | 12/1986 | Freedland . |
| 4,738,255 | 4/1988 | Goble et al. ............................ 606/232 |
| 4,750,492 | 6/1988 | Jacobs . |
| 5,051,250 | 5/1991 | Foster ................................. 606/147 |
| 5,105,648 | 4/1992 | Steiner et al. ............................ 29/751 |
| 5,111,681 | 5/1992 | Yasui et al. ............................ 29/751 |
| 5,116,340 | 5/1992 | Songer et al. ............................ 606/103 |
| 5,141,520 | 8/1992 | Goble et al. ............................ 606/232 |
| 5,143,500 | 9/1992 | Schuring et al. . |
| 5,175,911 | 1/1993 | Terrels et al. . |
| 5,236,445 | 8/1993 | Hayhurst et al. . |
| 5,258,015 | 11/1993 | Li et al. . |
| 5,258,016 | 11/1993 | DiPoto et al. . |
| 5,268,001 | 12/1993 | Nicholson et al. . |
| 5,269,809 | 12/1993 | Hayhurst et al. . |
| 5,300,082 | 4/1994 | Sharpe et al. ............................ 606/147 |
| 5,342,393 | 8/1994 | Stack . |
| 5,376,096 | 12/1994 | Foster ................................. 606/147 |
| 5,405,354 | 4/1995 | Sarrett ................................. 606/148 |
| 5,423,860 | 6/1995 | Lizardi et al. ............................ 606/232 |

FOREIGN PATENT DOCUMENTS

820812  4/1981  U.S.S.R. .

*Primary Examiner*—Gary Jackson

[57] ABSTRACT

The disclosure contemplates a device for cinching surgical sutures, an applicator for applying the device, a dispenser for dispensing the device, an endoscopic kit including the above and a method of use for the same.

15 Claims, 11 Drawing Sheets

SUTURE CINCHING APPARATUS

BACKGROUND

TECHNICAL FIELD

The present application relates to a suture cinching apparatus for cinching surgical sutures to retain the suture position during endoscopic and laparoscopic surgical procedures.

DESCRIPTION OF THE RELATED ART

In surgical operations it is well known that surgical sutures are applied to repair the body tissue. Such sutures generally are of the non-absorbable or the absorbable type and are generally applied with the use of surgical needles. If the sutures are non-absorbable, they may or may not be removed after an estimated predetermined healing period has passed. Absorbable sutures are absorbed gradually over time by coming in contact with moisture in the human body.

In many surgical procedures, application of sutures generally involves knotting or tying the suture after it is applied to the body tissue in order to retain its position with respect to the tissue and to maintain the tissue in the repaired position. In cases where the surgeon has full access to the operative site by virtue of a large incision, knotting the suture or applying knotting or equivalent devices is relatively simple due to the access provided by the incision.

In endoscopic and laparoscopic procedures, on the other hand, large incisions are avoided. In laparoscopic procedures surgery is performed in the interior of the abdomen through a small incision; in endoscopic procedures surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that instruments to be used in such procedures generally be both long and narrow.

In laparoscopic and endoscopic procedures surgical sutures are generally applied by directing and manipulating needled sutures through an aperture in the body or through elongated narrow tubes known as cannulae with the assistance of specially designed needle graspers, needle drivers, and the like. However, tying the sutures in such procedures can be relatively difficult due to the limited access afforded to the surgeon through the narrow tubes. In particular, since biocompatible, preferably bioabsorbable, sutures are generally used in such procedures it would be desirable to have available a cinching device and system that facilitates tying the sutures through the tubes in a manner to retain their position in the body tissue at least until the healing process is in full progress. The use of the term "endoscopic" herein contemplates endoscopic as well as laparoscopic procedures.

U.S. Pat. No. 4,291,698 to Fuchs et al. relates to a button for surgical applications in which a disk is provided having a slot which extends to a passage for clamping a thread therethrough within the circumference of the disk, and the passage is sealed by a clamping device for securing the thread firmly in the passage.

U.S. Pat. No. 4,750,492 to Jacobs relates to an apparatus for repairing torn animal body tissue in a single procedure wherein a suture is enclosed and clenched by an apparatus formed of biodegradable material.

Neither the button of the '698 patent nor the apparatus of the '492 patent are contemplated for application to body tissue during endoscopic or laparoscopic procedures whereby the suture may be cinched for tying relative to the body tissue through the long relatively narrow tubes used in such procedures. The present application relates to a suture cinching apparatus which includes an applicator for applying suture cinching devices in endoscopic, laparoscopic, and invasive procedures in a manner which is convenient, quick and simple in application. In addition, the present application relates to a particular type of suture cinching device and kit for applying same, whereby the suture cinching device is bioabsorbable upon contact with body moisture or is biocompatible.

SUMMARY

A device for cinching surgical sutures, an applicator for applying the device, a dispenser for dispensing the device and an endoscopic kit including the above are provided. The device for cinching comprises a first generally elongated member defining a generally longitudinal axis and a second generally elongated member defining a generally longitudinal axis and positionable at least partially within the first member with the generally longitudinal axis in alignment with the axis of the first member, the first member movable between a first position which permits reception of a surgical suture therebetween in a direction generally transverse to the longitudinal axis and a second position in engagement with the second member which cinches the suture therebetween.

The applicator has a handle portion and an elongated endoscopic tubular portion connected to the handle portion, the endoscopic tubular portion having a distal end defining an opening for reception of the first and second members in relative spaced position for reception of the suture therebetween. The applicator also has an actuating system for advancing the first member of the device distally toward the second member to cinch the suture when positioned therebetween and extending in directions generally transverse to the longitudinal axis of the first and second members, the actuating system being further adapted to eject the first and second members from the distal end of the applicator upon completion of the suture cinching procedure.

Also provided is a method of use for the above device, applicator and kit.

DETAILED DESCRIPTION OF THE PREFERRED EMBODIMENTS

Figure 1:
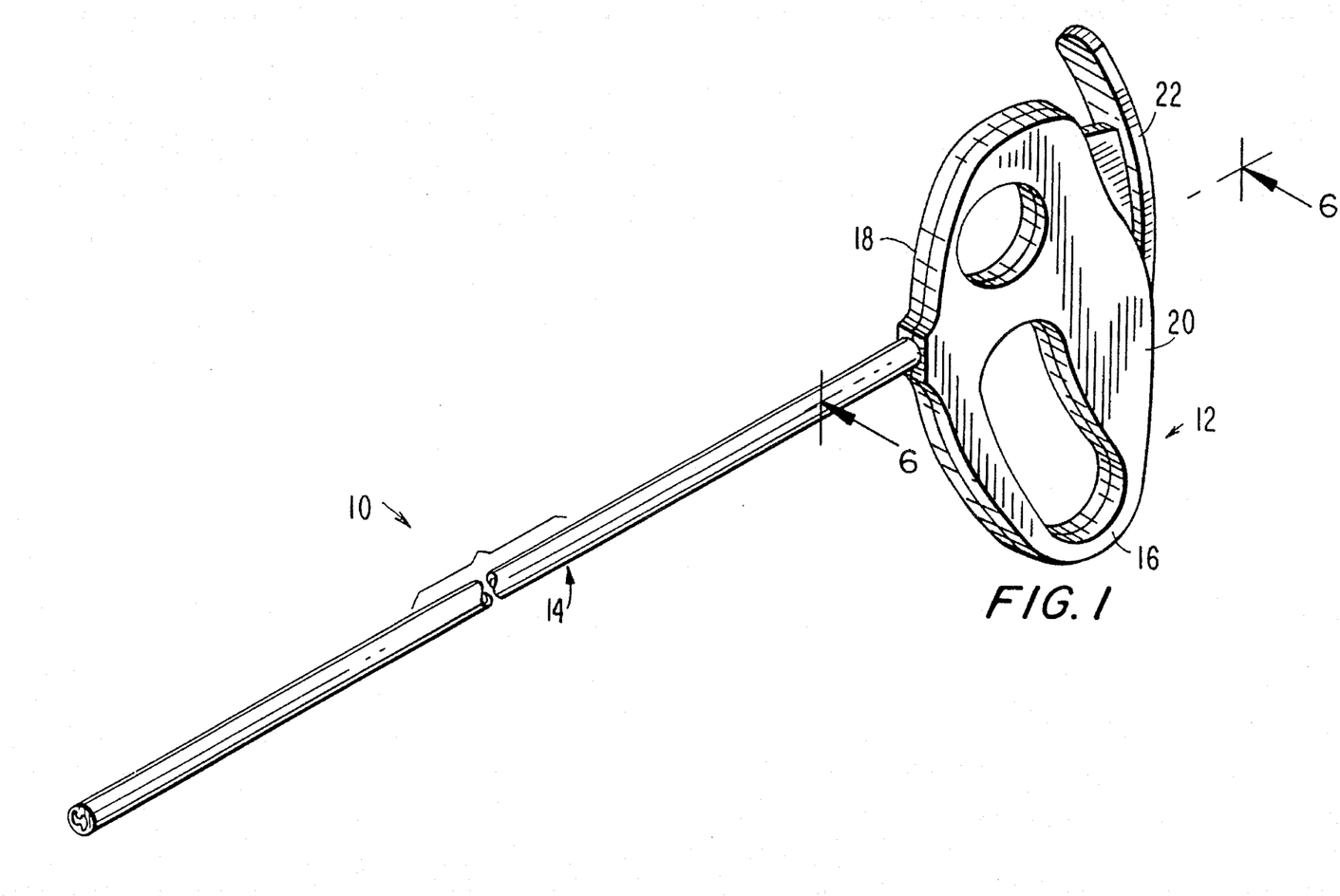
FIG. 1 is a perspective view of an applicator for applying a suture cinching device as disclosed herein.
Figure 2:
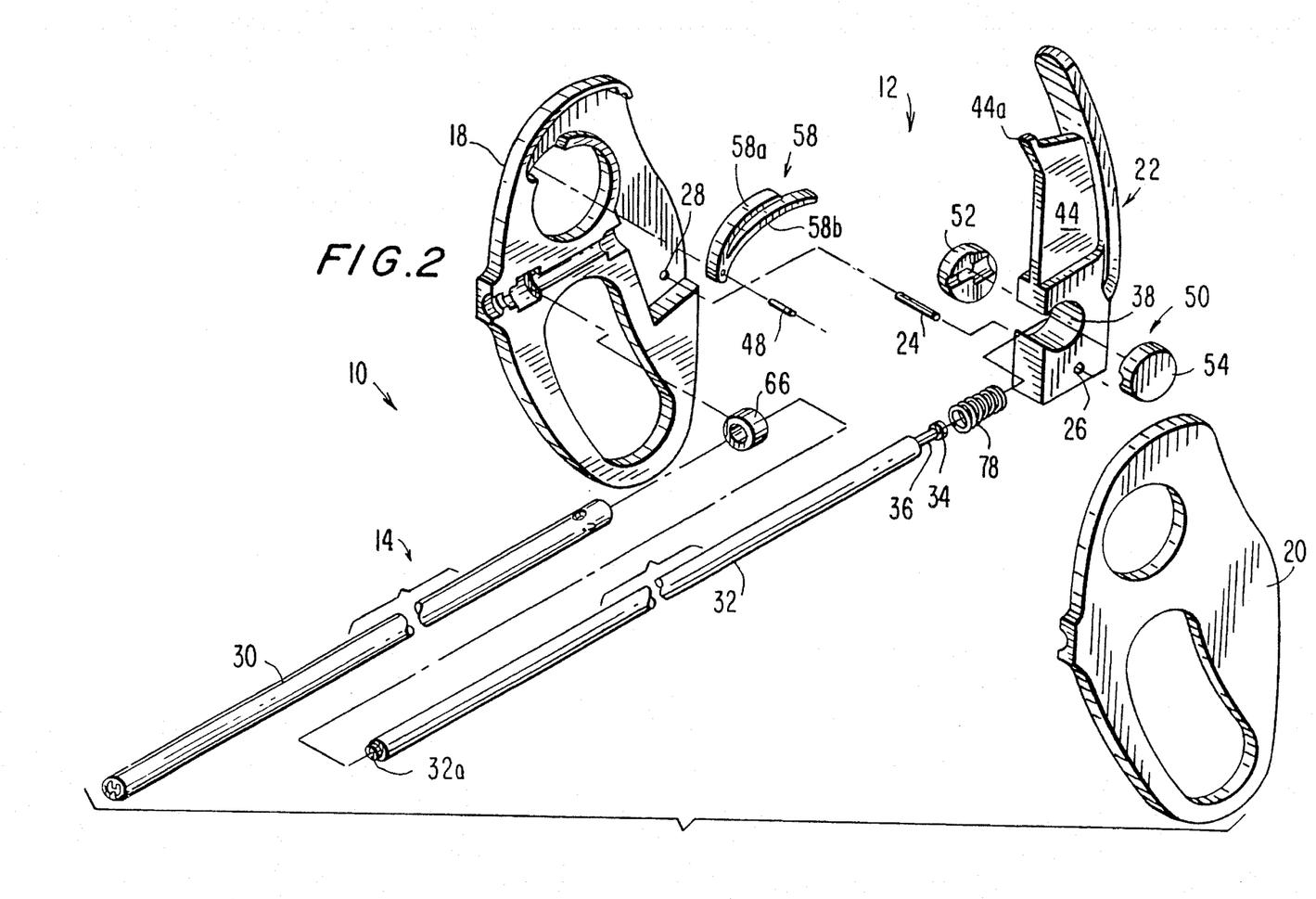
FIG. 2 is a perspective view, with parts separated for convenience of illustration, of the applicator of FIG. 1.

Referring initially to FIG. 1 in conjunction with FIG. 2 a preferred embodiment of the present applicator 10 for applying the present suture cinching device is disclosed. The applicator 10 includes handle section 12 and endoscopic section 14 through which the required components for manipulating the suture cinching device extend. In general, handle section 12 includes hand gripping portion 16 and pivotally movable lever 22 which controls the cinching procedure for cinching sutures with the suture cinching device, as well as the procedure to eject the suture cinching device from the applicator as will be described in greater detail below.

Handle section 12 is formed of two handle half sections 18,20 molded preferably of a plastic material such as polycarbonate. Handle sections 18,20 are shown separated in FIG. 2 and in assembled condition in FIG. 1. Assembly of the half sections 18,20 can be accomplished by suitable attachment techniques such as ultrasonic welding, adhesives, etc. Actuating lever 22 is pivotally mounted on pivot pin 24 positioned in aperture 26 and extending into respective apertures in half sections 18,20 for support through aperture 28 in half section 18 and a corresponding aperture in section 20 (not shown).

Endoscopic section 14 includes endoscopic outer tube 30 and inner push rod 32 slideable therein in distal and proximal directions. At the proximal end, push rod 32 includes a disc-shaped head 34 connected thereto by neck 36 and positioned within locking clip 50 formed of opposed complementary sections 52,54 and is disposed in a circular port 38 provided in actuating lever 22. The push rod 32 is movable distally along the axis of the endoscopic portion 14 in response to distal pivotal movement of the actuating lever 22. Locking clip 50 is thus permitted to rotate relative to the circular port 38 when actuating lever is pivotally advanced, thus providing a "universal joint" type connection between push rod 32 and actuating lever 22.

Figure 6:
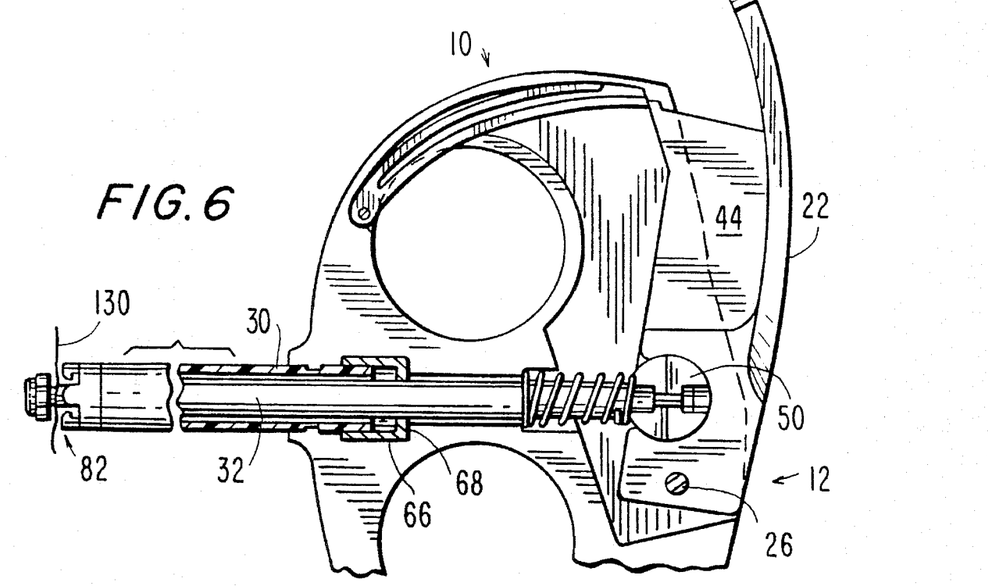
FIG. 6 is an elevational view, partially in cross-section, of the entire apparatus for cinching a suture, illustrating the handle section of the applicator at the proximal end and the suture cinching device at the distal end in open, ready to use, condition.
Figure 7:
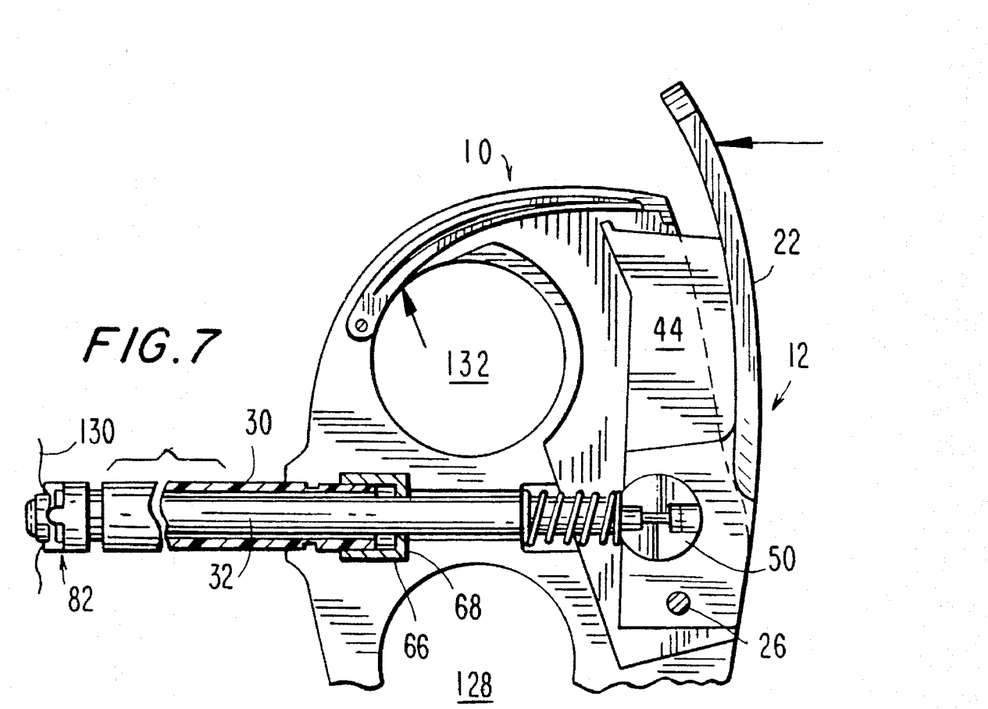
FIG. 7 is a view similar to FIG. 6 with the suture cinching actuating lever in a partially depressed condition which corresponds to a partial cinching of the suture within the suture cinching device at the distal end as shown.

Referring again to FIG. 2 in conjunction with FIGS. 6 and 7, actuating lever lock 58 is in the form of an arcuate "V" shaped leaf spring having upper arcuate leaf 58a and lower arcuate leaf 58b and mounted on pin 48 to housing half sections 18,20. Coil spring 78 positioned about the proximal end of push rod 32 provides resilient bias force against distal pivoting motion of actuating lever 22 causing lever 22 to return to its proximal rest position when released.

Figure 8:
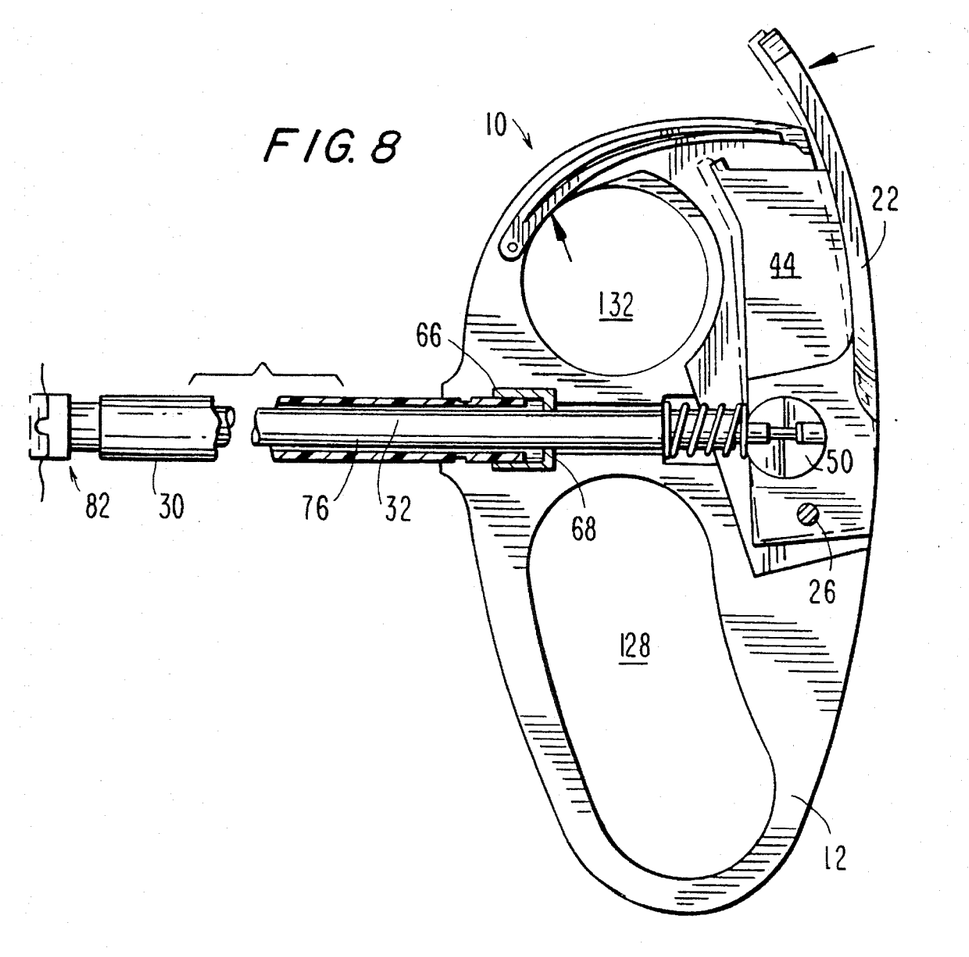
FIG. 8 is a view similar to FIG. 7 with the suture cinching actuating lever in a near fully depressed condition which corresponds to the fully cinched condition of the suture within the suture cinching device at the distal end as shown.

As best seen in FIG. 2 in conjunction with FIGS. 6, 7 and 8, elastomeric wiper seal 66 is generally circular and cup shaped and has its distal end positioned about and in engaged relation with the proximal end of outer tube 30. The proximal end of seal 66 includes an inwardly depending annular wiper flange 68 which engages and wipes push rod 32 as it moves proximally and distally as will be described. This wiper seal permits push rod 32 to slide distally and proximally while preventing insufflation gases from escaping from the patient's body through outer tube 30 and into the handle section 12, via the annular space 76 between push rod 32 and outer tube 30.

Figure 3:
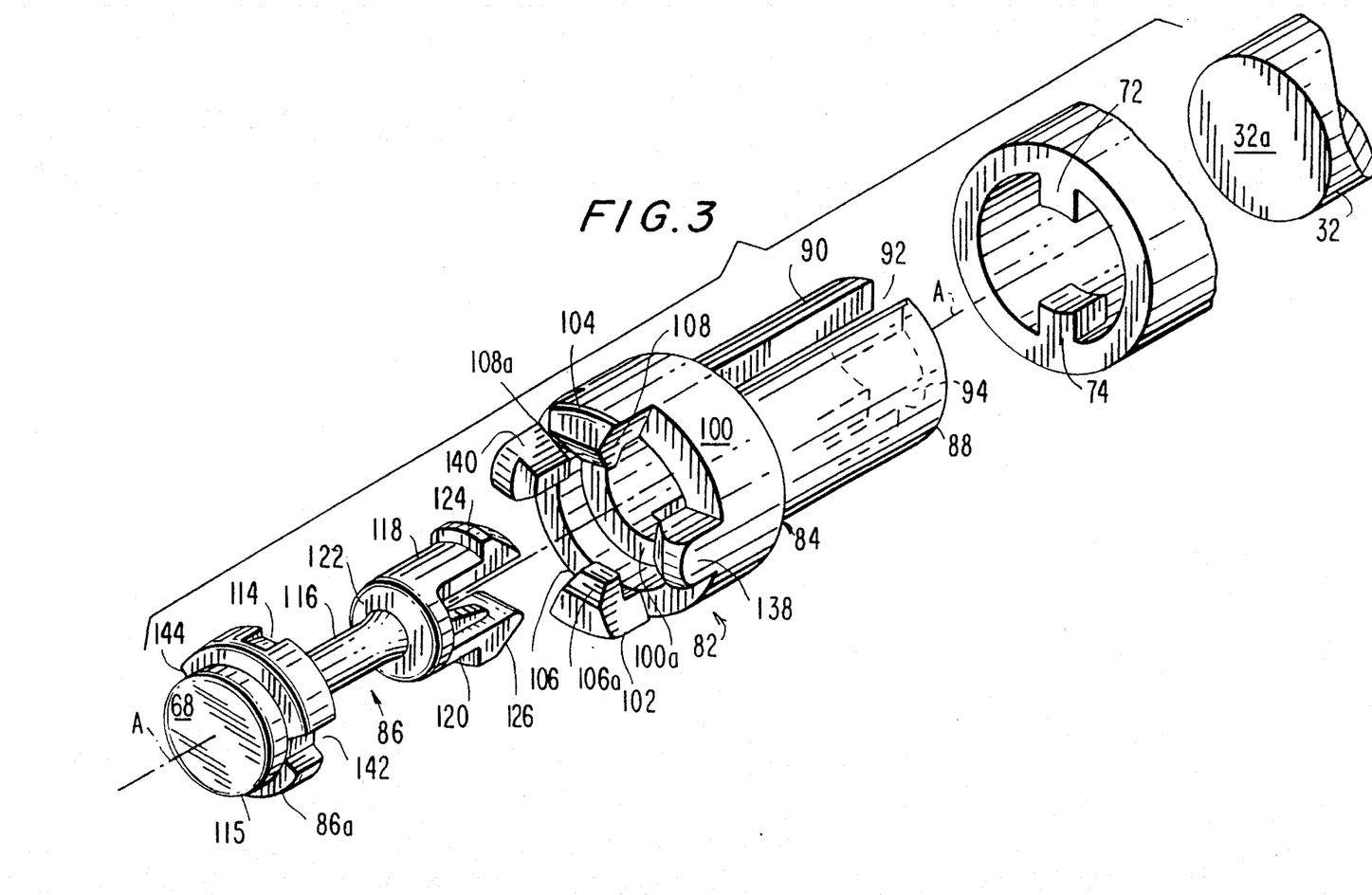
FIG. 3 is a perspective view, with parts separated for convenience of illustration, of a suture cinching device of the present application, positioned distally with respect to the distal end of the applicator.
Figure 5:
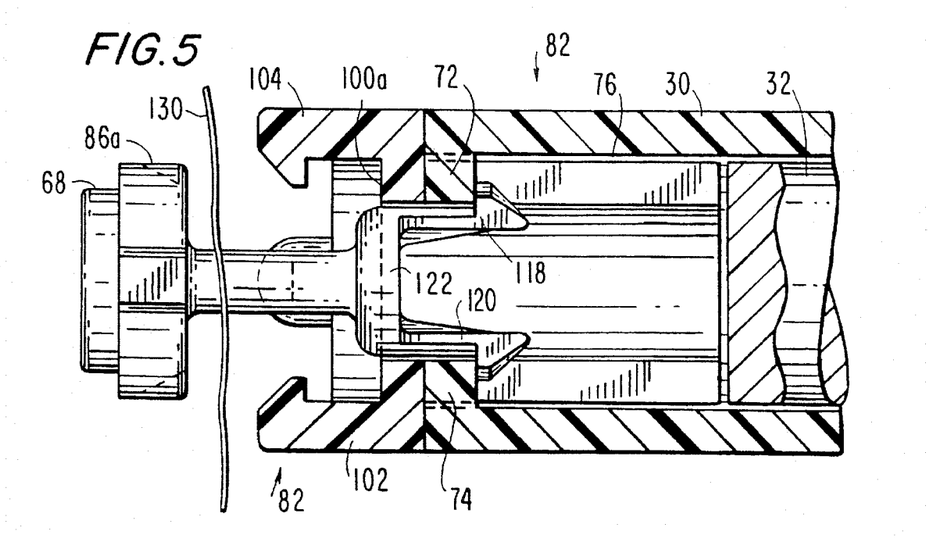
FIG. 5 is a partial cross-sectional view taken along lines 5—5 of FIG. 4.
Figure 9:
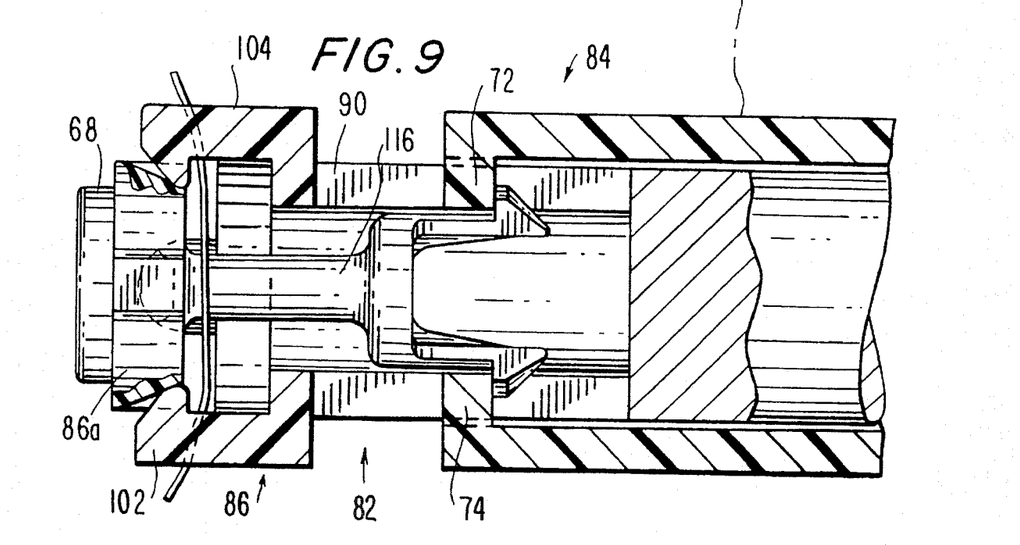
FIG. 9 is a partial cross-sectional view of the distal end of the suture cinching apparatus with the suture cinching device in partially closed condition corresponding to FIG. 7 just prior to cinching engagement of the suture.
Figure 10:
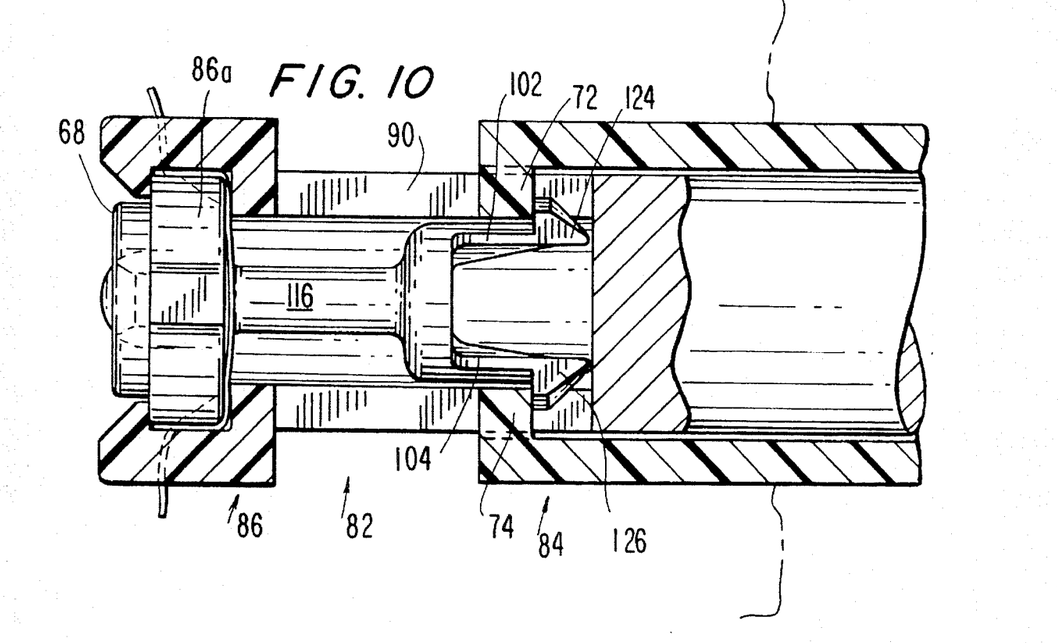
FIG. 10 is a partial cross-sectional view similar to FIG. 9, with the suture cinching device in a partially cinched condition corresponding to FIG. 8 just prior to closing.

Outer tube 30 includes inwardly depending flanges 72,74 at the distal end as best shown in FIGS. 3, 5 and 9. Depending flanges 72,74 are dimensioned and configured to engageably receive the legs of the suture cinching device as will be described in further detail below.

Figure 4:
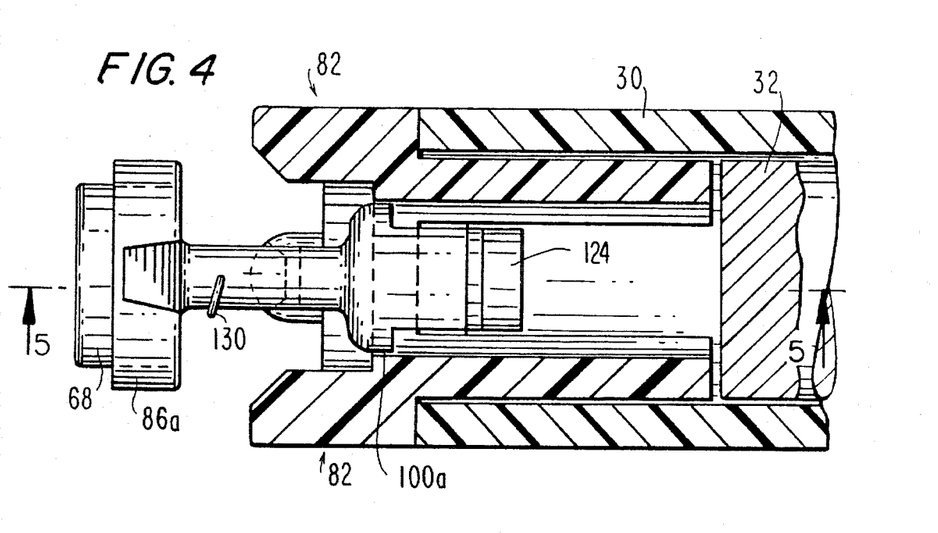
FIG. 4 is a partial cross-sectional view of the distal end of the applicator of FIG. 1 with the two-part suture cinching device in position therein and in the open position ready for use.

Suture cinching device 82 is shown in respective mutually perpendicular elevational views in FIGS. 4 and 5. While suture cinching device 82 may be made of any biocompatible material, it is preferably formed of a semi-rigid bioabsorbable material which may remain in the patient's body along with the bioabsorbable suture and ultimately absorbed by contact with moisture in the patient's body. By "semi-rigid" it is meant that while the particular bioabsorbable material of the suture cinching device is such that the material displays substantial resilient properties and characteristics, it can nevertheless be deformed and squeezed through a relatively narrow space to accomplish a particular result only to return to its normal unloaded shape when the force is released.

Bioabsorbable polymers which may be utilized for the sutures as well as for the suture cinching device 82 disclosed herein are well known. Such polymers may include polyhydroxyacids, polylactones, polycarbonates, polyanhydrides, polyesteramides, polyetheresters, polyorthoesters, polysaccharides, poly(alkylene oxide) containing polymers, and copolymers, terpolymers and blends thereof. Preferably, homopolymers or copolymers of glycolidelactide, trimethylene carbonate and/or dioxanone are employed.

Referring now to FIG. 3 in conjunction with FIGS. 4 and 5, suture cinching device 82 includes suture cinching base section 84 and flanged suture cinching button section 86. Suture cinching base section 84 is formed of cylindrical half sections 88,90 having slots 92,94 therebetween extending in the direction of the longitudinal axis A—A. Slots 92,94 are dimensioned for reception of inwardly depending flanges 72,74 at the distal end of tip end portion of outer tube 30. Suture cinching base section 84 also includes at its distal end, flanged head 100 having legs 102,104 at its distal end with inwardly extending flanges 106,108. Suture cinching base section 84 of suture cinching device 82 also includes distally extending positioning flanges 138,140.

In FIG. 3, suture cinching button section 86 includes disc-like suture cinching button 86a with disc-like portion 68 extending distally. Suture cinching button 86a is in the shape of a disc having at least two slots defining sloped surfaces 114, 116 positioned and extending toward the proximal side thereof about 180° apart from each other and corresponding to the locations of flanges 106,108. Extending proximally from suture cinching button 86a is neck 116 to which is connected a pair of attaching legs 118,120 via intermediate circular base section 122. Each leg 118,120 has outwardly extending attaching flange 124,126 respectively connected to the proximal end and 180° apart from each other for resilient locked engagement with inwardly depending flanges 72,74 of the outer tube 30.

The major components of the applicator are preferably constructed of a rigid polycarbonate material such as LEXAN brand plastic material by General Electric Company. Such components include handle section 12, outer tube 30, and actuating handle 22. Components such as push rod 32 and the pivot pins are made of a substantially more rigid material such as stainless steel. Bias spring 78 is made of steel and elastomeric seal 66 is made of a suitable elastomer material. Alternative suitable materials may be substituted.

The operation of the suture cinching device applicator and the suture cinching device will now be described. During the course of the endoscopic or laparoscopic procedure the surgeon has complete control of the applicator, the grip and the direction of movement of the surgical suture 130 which is shown in FIGS. 4–12. All control is accomplished through the openings in the body with known graspers and other endoscopic laparoscopic equipment. At such time that cinching of the suture is necessary, the outer endoscopic tubular portion 14 of the applicator will have been inserted into an opening in the patient's body through a cannula tube which forms part of a device known as a cannula assembly and appropriate measures will have been taken to insufflate the body cavity where necessary and to provide seals to prevent loss of insufflation pressure through any openings in the equipment. Given the fact that the surgeon will be applying and manipulating the suture through an opening in the patient's body other than the opening in which the present applicator will have been inserted and with other application and manipulation equipment, the operation of the suture cinching device and the application to the suture within the patient's body will now be described.

Figures 14, 15, 16, 17:
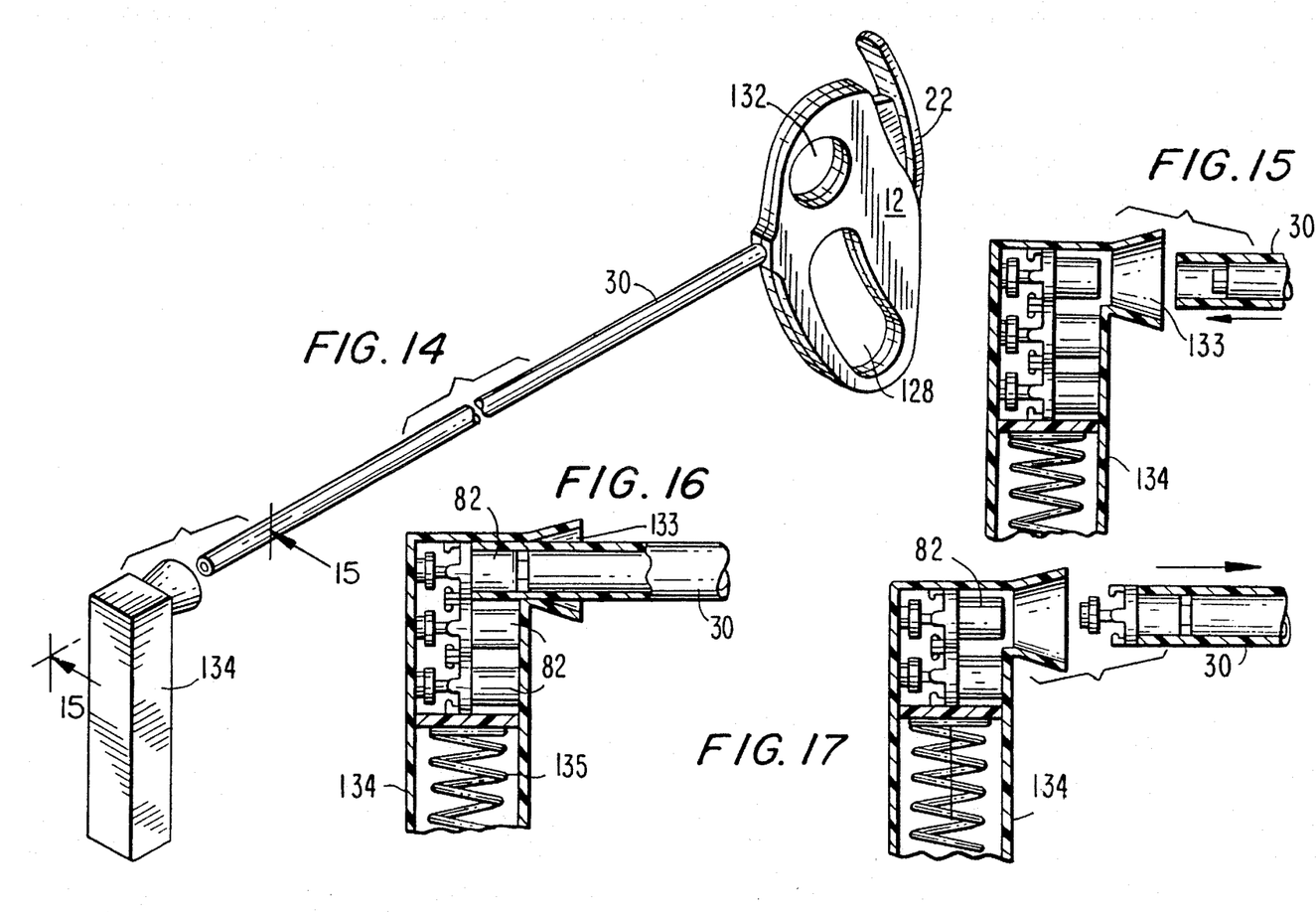
FIG. 14 is a perspective view of the applicator of FIG. 1 shown in position for attachment to a suture cinching device from a spring biased dispenser of such devices.
FIG. 15 is a partial cross-sectional view taken along lines 15—15 of FIG. 14 showing the distal tip of the applicator just prior to entry into the suture cinching device dispenser.
FIG. 16 is a partial cross-sectional view similar to FIG. 15 with the applicator tip portion in position for actual reception of a suture cinching device within the dispenser.
FIG. 17 is a partial cross-sectional view similar to FIG. 15 illustrating the distal tip portion of the applicator being withdrawn from the dispenser with the suture cinching device snapped in position for operation.

Referring to FIG. 14, the surgeon grips the handle 12 of the applicator and inserts three fingers through elongated opening 128 and the index finger through circular opening 132. Dispenser 134 contains a number of suture cinching devices 82 as shown in FIG. 15 which are maintained in a row and biased upwardly toward opening 133 by coil spring 135 such that when a suture cinching device is removed the remaining devices will be moved upwardly such that the next device will be in position for removal. In FIGS. 14–17, the removal of a suture cinching device from the dispenser is illustrated. Initially, the actuating lever 22 is in a locked position thus preventing it from being squeezed toward the handle 12 by the interference between lower leaf spring 58b of lever lock 58 and lock tab 44a of actuating lever 22. Thus unwanted inward movement of actuating lever 22 is prevented until the surgeon intentionally lifts the arcuate lower leaf spring 58b against its normal bias force and out of the interference relation by upward engaged movement of the surgeon's index finger.

The distal tip end of the instrument is then inserted into the spring loaded dispenser as shown in FIGS. 14 and 15 permitting inwardly depending flanges 72,74 to slide within slots 92,94 formed between cylindrical half sections 88,90 until flanges 124,126 of legs 118,120 engage the inwardly depending flanges 72,74 as best shown in FIG. 5. Then, as shown in FIG. 17, the applicator 10 is removed from the dispenser 134 with a suture cinching device 82 loaded into its distal end. At this stage, the suture cinching base section 84 and the suture cinching button section 86 of the suture cinching device 82 are assembled as shown in FIGS. 4 and 5, i.e. in spaced relation. Thus, at this stage the suture cinching device 82 is positioned at the distal tip of the applicator 10 and is ready for application, while the remaining suture cinching devices within dispenser 134 have been moved upwardly one position by coil spring 136 for removal by the applicator in the next sequence of the procedure.

It should be noted that the dispenser is optional. Alternatively, a number of suture cinching devices 82 could be pre-loaded into some portion the applicator such as endoscopic portion 14.

The outer tube 30 of applicator 10 has the suture cinching device 82 attached thereto at the tip end as shown in FIGS. 4 and 5, i.e. ready for application. At this, stage suture 130 may be placed between base section 84 and button section 82 and pressure may be applied to partially bring base 84 and button 82 together, i.e., a "cocked position" in which suture 130 is caught between the two sections as shown in FIGS. 7 and 9, but can still move due to the fit between inward slots 142, 144 on button 86 and flanges 138, 140 on base section 84. In this way, the manual manipulation required to place the suture between the button 86 and base 84 may be accomplished extracorporeally.

Alternatively, the tube 30 is inserted into the trocar cannula (not shown) to the operative site where the suture 130 is positioned and manipulated by appropriate suture application equipment. The tube is then manipulated along with the independent manipulation of the suture 130 until the suture is appropriately positioned between the suture cinching button section 86 and the suture cinching base section 84 of the suture cinching device 82 and approximately perpendicular to the axis A—A of the suture cinching device 82. As described above, suture cinching base section 84 of suture cinching device 82 also includes distally extending positioning flanges 138,140 as shown in FIG. 3.

As explained above, each flange 138,140 is dimensioned for reception within slots 142,144 of the suture cinching button 86a when the suture cinching base section 84 is made to slide distally into engaged reception with the suture cinching button section 86. In addition, suture cinching button 86a includes circular extension 68 extending distally to provide a substantially even surface at the distal end face as shown in the elevational view of FIG. 12 and in the end view of FIG. 13.

With suture 130 positioned as shown in FIGS. 4 and 5, i.e. ready for cinching, the surgeon manipulates lower section 58b of leaf spring 58 upwardly thereby permitting actuating lever 22 to be depressed distally toward handle section 12 in pivoted motion about pin 60 and against spring 62. This movement simultaneously causes universal locking clip 50 to rotate within circular port 38 and to move distally thus pushing push rod 32 distally. The forward movement of push rod 32 causes distal face 32a to engage circular half sections 88,90 of suture cinching base section 84 to forcibly displace the base section distally until disc-shaped suture cinching button 86a is received between inwardly extending flanges 106,108 of legs 102,104 with the sloped surfaces 106a, 108a slideably engaging and camming up the correspondingly sloped surfaces 110,114 of disc-like suture cinching button 86a. Thus, the actual suture cinching procedure is terminated intracorporeally and the suture cinching device is in the condition shown in FIG. 10 with the suture cinched between the cinching button 86a and surface 100a on flanged head 100 of the base section 84 when in a fully fired position.

Figure 11:
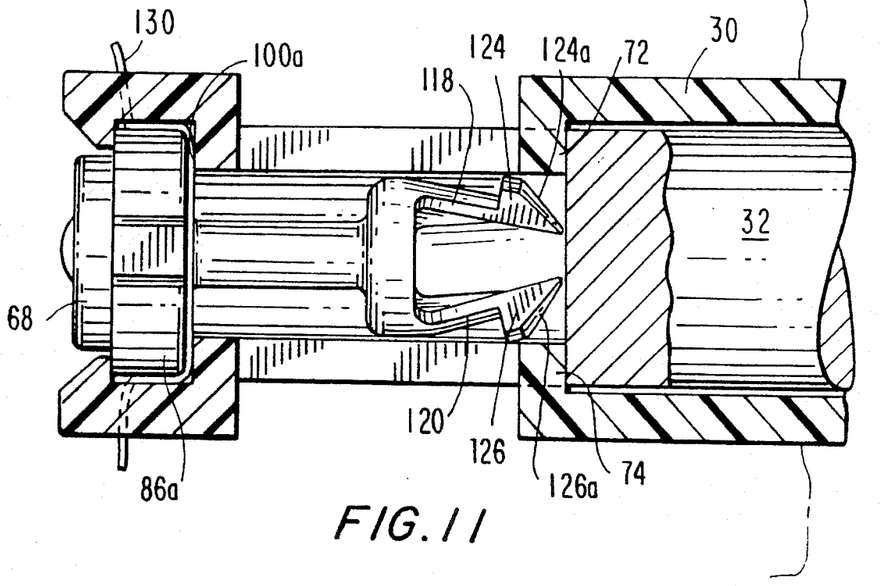
FIG. 11 is a partial cross-sectional view similar to FIG. 10 with the suture cinching device in the fully cinched condition and in the nearly ejected position corresponding to the position of the actuating lever shown in dashed lines in FIG. 8.
Figure 12:
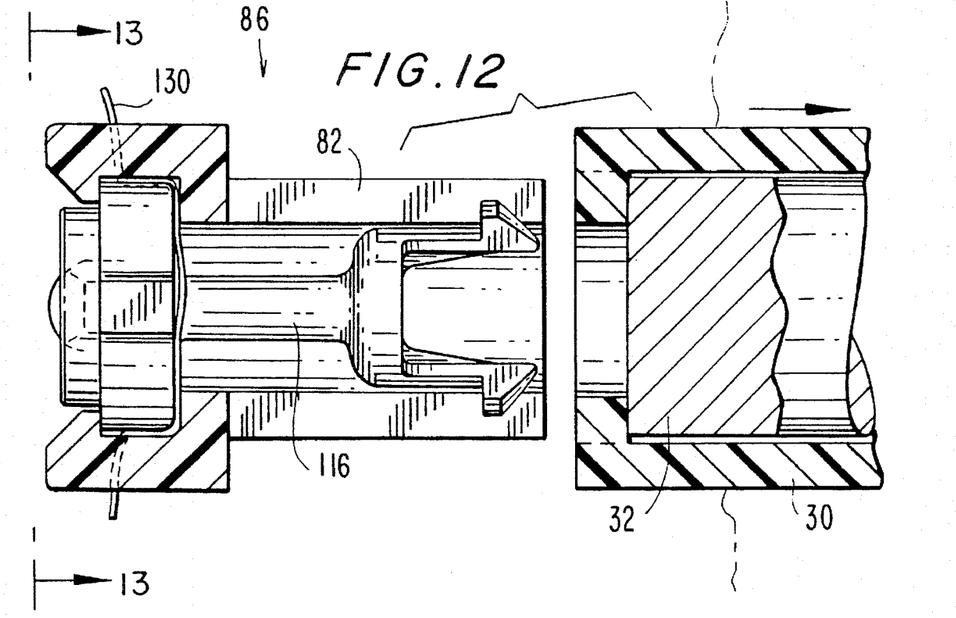
FIG. 12 is a partial cross-sectional view similar to FIG. 11 with the suture cinching device fully ejected from the applicator with the suture cinched therein.
Figure 13:
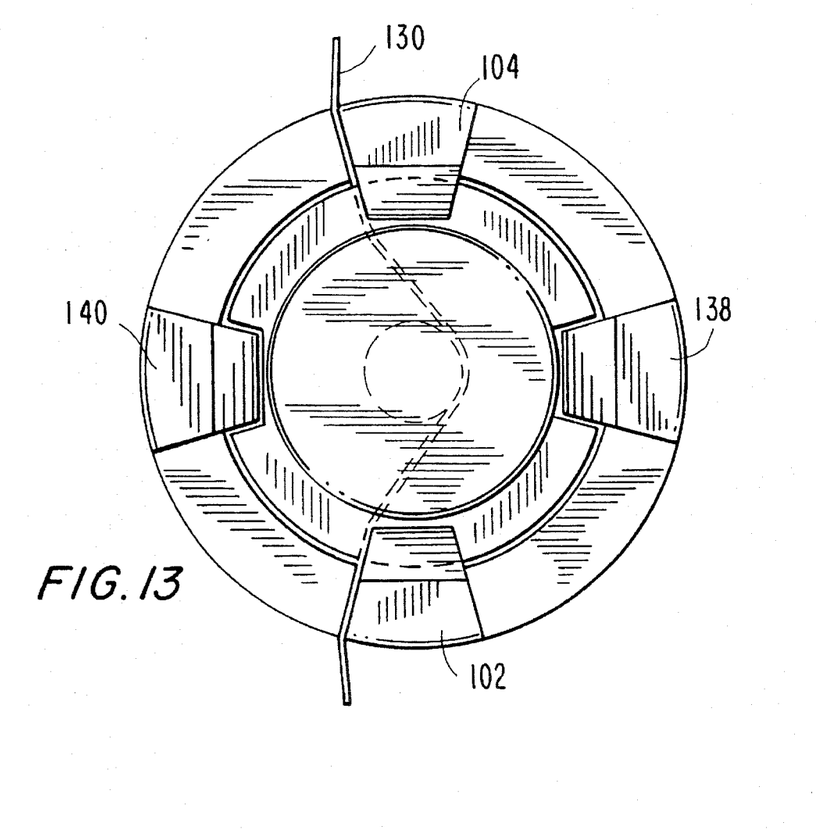
FIG. 13 is a front elevational end view taken along lines 13—13 of FIG. 11 of the suture cinching device with the suture cinched therein.

Referring now to FIG. 11, with continued distal movement corresponding to the lever portion shown in dashed lines in FIG. 8, the push rod 32 further engages flanges 124,126 of legs 118,120 to remove the assembled suture cinching device as shown. This further movement of the push rod 30 causes engagement and deformation of legs 120,124 and flanges 124,126 as shown in FIG. 11. This deformation is possible due to the semi-rigid character of the bioabsorbable or biocompatible material which forms the suture cinching device. The deformed surfaces 124a, 126a of the flanges 124,126 are then free to move past the corners of flanges 72,74 of outer tube 30 causing ejection of the suture cinching device when legs 118,120 return to their original shape as shown in FIG. 12.

The applicator tube is then removed from the trocar in the patient's body for a repeat procedure with the next suture cinching device in the dispenser 134. Generally, the suture cinching device 82 will remain in the patient's body with the suture gripped between the components as shown in FIG. 12. This permits the suture and the cinching device to be locked into position relative to the body tissue and the suture cinching device prevents further movement of the suture through the body tissue by engagement therewith to promote healing.

Figures 18, 19:
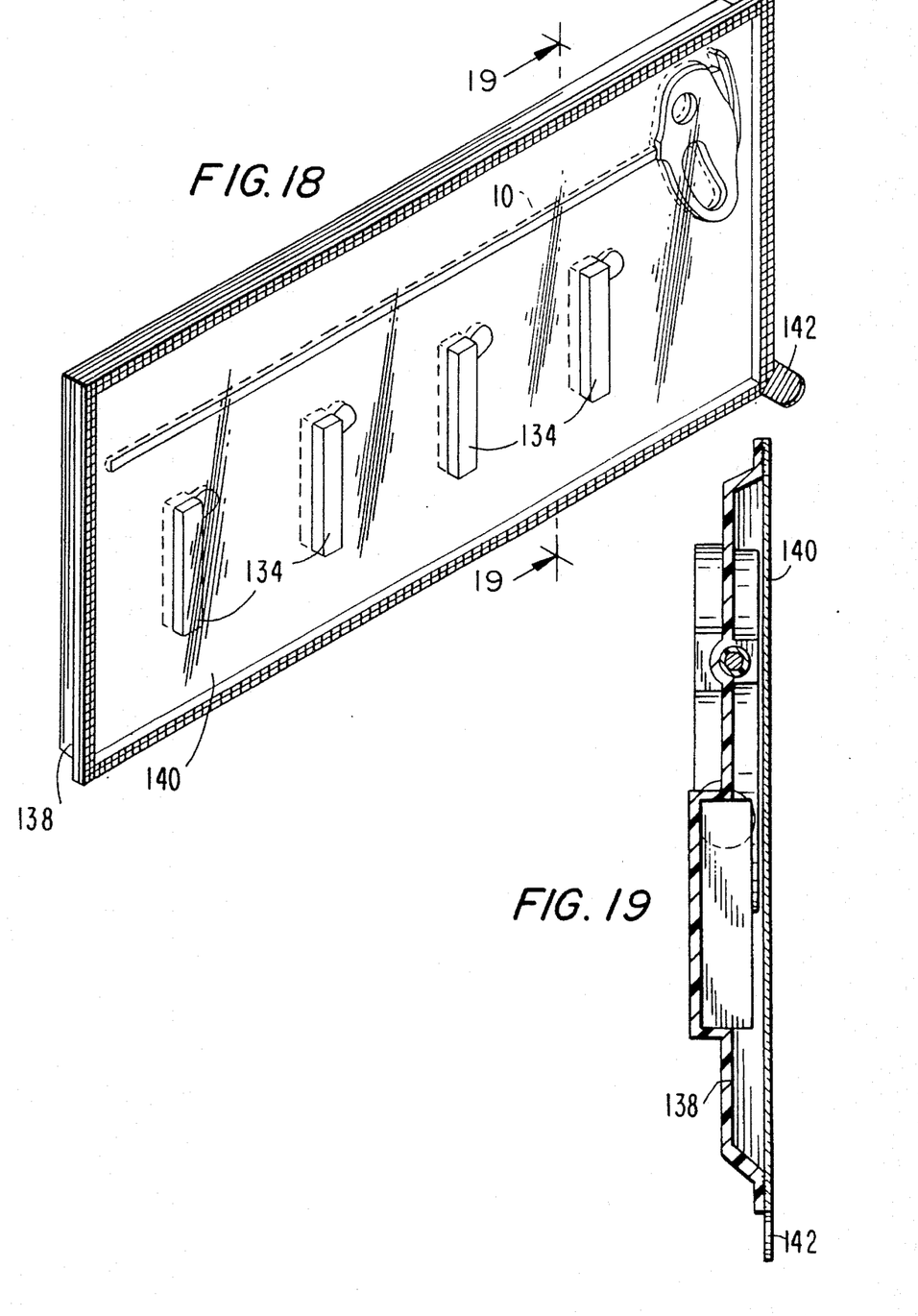
FIG. 18 is a perspective view of a kit incorporating the applicator of the present embodiment and several suture cinch device dispensers all provided in a convenient blister package having a tear-off cover strip.
FIG. 19 is a partial cross-sectional view taken along lines 19—19 of FIG. 18.

Referring now to FIG. 18, there is illustrated a perspective view of a kit which incorporates the applicator 10 as disclosed herein along with four dispensers 134 for containing and dispensing suture cinching devices 82 of the present application. The entire kit conveniently contains blister-type backing member 138 with appropriately shaped indentations for reception of the applicator 10 and the suture cinching device dispensers 134 and a convenient transparent cover tear strip 140. During the surgical procedure, the surgeon may remove the tear strip by lifting tear tab 142 thereby providing access to the applicator 10 and the suture cinching device dispensers 134 for application of the suture cinching devices as described.

In the description of the preferred embodiments presented hereinabove, the first generally elongated suture cinching means contemplates suture cinching base section 84 as shown in FIG. 3 and the second generally elongated suture cinching means contemplates the suture cinching button section 86 also shown in FIG. 3. In particular, the suture cinching button section 86 includes the suture cinching button 86a, the neck 116 and legs 118,120.

What is claimed is:

1. Device for cinching surgical sutures, which comprises:
   a) first generally elongated member defining a generally longitudinal axis; and having a generally elongated neck portion having a distal end and a proximal end, and a head portion connected to the distal end of the neck portion, the head portion, the head portion having at least two extension flanges and
   b) second generally elongated member defining a generally longitudinal axis and positionable at least partially within the first member with the generally longitudinal axis in alignment with the axis of the first member, the first member movable between a first position which permits reception of a surgical suture between the first and second member in a direction generally transverse to the longitudinal axis and a second position in engagement with wherein said at least two extension flanges are the second member which cinches the suture between the first and second members.

2. The device for cinching surgical sutures according to claim 1 wherein the second member comprises an elongated neck portion having a proximal end and a distal end, a pair of locking legs connected to the proximal end of the neck portion for engaged reception by the first member, and a suture cinching head connected to the distal end of the neck portion for cinched reception of a surgical suture between the cinching head and the first member.

3. The device for cinching surgical sutures according to claim 2 wherein the head portion of the first member defines a generally annular shaped member having an inner open aperture for engaged reception of at least a portion of the head portion of the first member and at least two extensions at distal end which define at least two surface portions which generally complement corresponding respective surface portions on said second member to facilitate the engaged reception of the first member with the second member with the suture therebetween.

4. The device for cinching surgical sutures according to claim 3 wherein the neck portion of the first member defines at least two generally elongated opposed slots extending in the longitudinal direction and dimensioned for reception of corresponding opposed depending flange members of an applicator for applying the suture cinching device, the flanges being dimensioned for engaged reception by the leg portions of the second member for positioning the suture cinching device on the applicator for application to body tissue.

5. The device for cinching surgical sutures according to claim 4 wherein the suture cinching head of the second member is dimensioned for reception within an annular wall portion of the first member for cinching the suture therebetween.

6. The device for cinching surgical sutures according to claim 5 wherein the cinching head of the second member comprises a disc shaped member defining opposed spaces at the periphery thereof for reception of correspondingly configured and dimensioned locator extensions positioned on the first member.

7. The device for cinching surgical sutures according to claim 6 wherein the first and second members are formed of a bioabsorbable material.

8. Apparatus for cinching surgical sutures in a surgical procedure which comprises:
   a) a suture cinching device including:
      i) a first generally elongated suture cinching member defining a generally longitudinal axis; and
      ii) a second generally elongated suture cinching member defining a generally longitudinal axis and positionable at least partially within the first suture cinching member with the generally longitudinal axis in alignment with the axis of the first suture cinching member, the first suture cinching member movable between a first position which permits reception of a surgical suture therebetween in direction generally transverse to the longitudinal axes in a second position in engagement with the second member in which the suture is cinched therebetween;
   b) an applicator having a handle portion and an elongated tubular portion connected to the handle portion, the tubular portion having a distal end defining an opening for reception of the first and second members in relative spaced position for reception of the suture therebetween; and
   c) an actuating system in the applicator for advancing the first member distally toward the second member to cinch the suture when positioned therebetween and extending in a direction generally transverse to the longitudinal axis of the first and second members, the actuating system being further adapted to eject the first and second members from the distal end of the applicator upon completion of the suture cinching procedure.

9. The apparatus for cinching surgical sutures according to claim 8 further comprising at least one suture.

10. The apparatus for cinching surgical sutures according to claim 8 wherein the suture cinching device is made of a bioabsorbable material.

11. A kit for cinching surgical sutures in surgical procedures, which comprises:
   a) at least one dispenser containing a plurality of suture cinching devices for dispensing, each suture cinching device including:
      i) a first generally elongated member defining a generally longitudinal axis; and
      ii) a second generally elongated member defining a generally longitudinal axis and positionable at least partially within the first member, with the generally longitudinal axis in alignment with the axis of the first member, the first member movable from a first position which permits reception of a surgical suture therebetween in the direction generally transverse to the longitudinal axis and a second position in engagement with the second member which cinches the suture therebetween;
   b) an applicator having a handle portion and an elongated portion connected to the handle portion, the elongated portion having a distal end defining an opening for reception of the first and second members in relatively spaced relation; and
   c) an actuating system in the applicator for displacing the first member toward the second member to cinch the suture when positioned therebetween and extending in the direction generally transverse to the longitudinal axes of the first and second members, the actuating system being further adapted to eject the first and second members from the distal end of the applicator upon completion of the suture cinching procedure.

12. The kit according to claim 11 further comprising a package containing at least one such applicator and at least one such dispenser, the package having a protective cover for protecting and displaying the applicator and the at least one dispenser.

13. The kit according to claim 11 wherein said package contains at least three of said dispensers.

14. The kit according to claim 11 wherein the suture cinching devices are made of a bioabsorbable material.

15. The kit according to claim 11 further comprising a supply of surgical sutures.

* * * * *